United States Patent
Johnson

(12) 
(10) Patent No.: US 11,051,635 B2
(45) Date of Patent: Jul. 6, 2021

(54) PILLOW FOR TREATING AND PREVENTING PLAGIOCEPHALY

(71) Applicant: Kasey Marie Johnson, Pleasant Hill, IA (US)

(72) Inventor: Kasey Marie Johnson, Pleasant Hill, IA (US)

( * ) Notice: Subject to any disclaimer, the term of this patent is extended or adjusted under 35 U.S.C. 154(b) by 6 days.

(21) Appl. No.: 16/372,630

(22) Filed: Apr. 2, 2019

(65) Prior Publication Data

US 2019/0298082 A1 Oct. 3, 2019

Related U.S. Application Data

(60) Provisional application No. 62/651,820, filed on Apr. 3, 2018.

(51) Int. Cl.
*A47D 15/00* (2006.01)
*A47G 9/10* (2006.01)
*A61F 5/01* (2006.01)

(52) U.S. Cl.
CPC ......... *A47D 15/008* (2013.01); *A47G 9/1009* (2013.01); *A47G 9/1081* (2013.01); *A61F 5/01* (2013.01); *A47G 2009/1018* (2013.01)

(58) Field of Classification Search
CPC .. A47D 15/008; A47G 9/1009; A47G 9/1081; A47G 2009/1018; A61F 5/01
See application file for complete search history.

(56) References Cited

U.S. PATENT DOCUMENTS

| | | | | |
|---|---|---|---|---|
| 5,937,461 | A * | 8/1999 | Dombrowski | A47D 15/003 5/655 |
| 6,052,849 | A * | 4/2000 | Dixon | A47D 15/008 5/643 |
| 6,052,850 | A * | 4/2000 | Salido | A47G 9/10 5/644 |
| 6,266,832 | B1 * | 7/2001 | Ezell | A47G 9/10 297/219.12 |
| 6,536,058 | B1 * | 3/2003 | Chang | A47G 9/1009 5/636 |
| 7,810,501 | B2 * | 10/2010 | Rogers | A61F 5/05891 128/845 |
| 8,332,978 | B2 * | 12/2012 | Warnock | A61G 7/072 5/655 |
| 8,590,536 | B2 * | 11/2013 | Tullous | A61F 5/05891 128/845 |
| 8,640,289 | B2 * | 2/2014 | Reeder, Jr. | A47D 13/08 5/640 |
| 10,667,627 | B2 * | 6/2020 | Degrazia | A61G 7/05723 |
| 2002/0153753 | A1 * | 10/2002 | Kassai | B60N 2/806 297/216.11 |
| 2003/0145384 | A1 * | 8/2003 | Stelnicki | A47D 13/08 5/655 |
| 2009/0070938 | A1 * | 3/2009 | Kell | A61F 5/05891 5/644 |

(Continued)

*Primary Examiner* — Nicholas F Polito
*Assistant Examiner* — George Sun
(74) *Attorney, Agent, or Firm* — Christopher A. Proskey; BrownWinick Law Firm

(57) ABSTRACT

In general, example embodiments are drawn to a pillow having a body with a neck support and at least one arm extending from a first end of the neck support to a second end of the neck support, the at least one arm having forming a center void. In example embodiments, a cover may be provided over or around the body.

24 Claims, 19 Drawing Sheets

(56) References Cited

U.S. PATENT DOCUMENTS

| | | | |
|---|---|---|---|
| 2009/0178202 A1* | 7/2009 | Kovalyak | A47C 20/026 5/655 |
| 2010/0242180 A1* | 9/2010 | Warnock | A61F 5/05891 5/637 |
| 2010/0275373 A1* | 11/2010 | Kaplan | A41B 13/06 5/494 |
| 2011/0056023 A1* | 3/2011 | Weeks | A47D 15/008 5/652 |
| 2011/0162657 A1* | 7/2011 | Tullous | A47D 15/008 128/845 |
| 2013/0111661 A1* | 5/2013 | Furuland | A47D 9/005 5/93.1 |
| 2016/0286964 A1* | 10/2016 | Lange | A47C 7/383 |
| 2017/0095096 A1* | 4/2017 | Mandell | A47G 9/10 |
| 2017/0265647 A1* | 9/2017 | Galloway | A47G 9/0246 |
| 2017/0318865 A1* | 11/2017 | Karnati | A47D 13/02 |
| 2018/0199731 A1* | 7/2018 | Starr | A47D 9/00 |
| 2018/0344042 A1* | 12/2018 | Melcher | A47G 9/1081 |
| 2019/0254356 A1* | 8/2019 | Clores | A47G 9/1045 |

\* cited by examiner

PILLOW FOR TREATING AND PREVENTING PLAGIOCEPHALY

CROSS-REFERENCE TO RELATED APPLICATIONS

This application claims the benefit of U.S. Provisional Patent Application No. 62/651,820 which was filed with the United States Patent and Trademark Office on Apr. 3, 2018, the entire contents of which is incorporated by reference.

BACKGROUND

1. Field

Example embodiments relate to a pillow usable for treating and/or preventing plagiocephaly.

2. Description of the Related Art

Many healthcare professionals suggest that laying an infant on his or her face increases the risk of Sudden Infant Death Syndrome (SIDS). To avoid this, healthcare professionals urge parents to place infants on their backs while resting or sleeping. Having infants sleep on their backs does have some drawbacks. For example, because infants have relatively weak neck muscles most do not have the strength to move their heads from side to side. Thus, an infant's head may remain tilted to one side while the infant is lying on his or her back. This is often what causes Torticollis in infants (referred to as "acquired Torticollis."). This can gradually cause a deformation in the back of the skull called plagiocephaly (i.e. a misshapen head). Over time, this can result in a pronounced protrusion on one side of the child's head accompanied by a relatively large flat spot on the other side of the head. FIG. 1, for example, illustrates a child's head 10 with a flattened area 12 and a protrusion 38. As a child reaches about 6 months old, the bones in the head begin to harden and permanently attach along the sutures and fontanelles. Thus, after about 6 months, the shape of the head remains more constant. At this time, a child having deformational plagiocephaly may have a skull that is relatively hardened. To correct the shape of the skull, the child may be required to wear a helmet which applies pressure to the cranial bones to achieve a more desired shape. However, helmets are generally uncomfortable for children to wear. In addition, helmets are extremely costly and many times they are not covered by insurance. Another disadvantage of helmets is that they require significant maintenance to continually shape and mold the child's head. As such, a new method or device to prevent or treat plagiocephaly is desired.

SUMMARY

In general, example embodiments are drawn to a pillow having a body with a neck support and at least one arm extending from a first end of the neck support to a second end of the neck support, the at least one arm forming a center void. In example embodiments a cover may be on or enclose the body.

In accordance with example embodiments, a method of treating plagiocephaly may include providing a pillow having at least one arm and an open center, providing a baby having a head that has an unaffected portion and an affected portion of the head, placing the pillow on a resting surface, placing the baby on the resting surface adjacent the pillow, and placing the baby's head on the pillow in such a manner that the unaffected portion of the head engages and is supported by the at least one arm of the pillow in such a manner that the affected portion of the head is raised above the resting surface thereby allowing the affected portion of the head to naturally reform without interference by the resting surface.

In accordance with example embodiments, a method of treating plagiocephaly may include providing a pillow having at least one arm and an open center, providing a baby having a head that has an unaffected portion and an affected portion, placing the pillow on a resting surface, placing the baby on the resting surface adjacent the pillow, placing the baby's head on the pillow such that the arm of the pillow engages the unaffected portion of the baby's head in at least two separate locations such that the affected portion of the head is raised above the resting surface thereby allowing the affected portion of the head to naturally reform without interference by the resting surface.

In accordance with example embodiments, a kit for treating plagiocephaly may include a first pillow having an arm and an open center, the first pillow having a first shape, and a second pillow having an arm and an open center, the second pillow having a second shape different from the first shape. In example embodiments the first pillow and second pillow may be used to support a baby's head to treat plagiocephaly, the first pillow and second pillow may engage the baby's head at different points of contact thereby allowing an affected portion of the head of the baby to naturally reform, and when the baby's head is placed on the first pillow or second pillow an affected portion of the baby's head is raised above a resting surface thereby allowing the affected portion of the head to naturally reform without interference by a resting surface.

BRIEF DESCRIPTION OF THE DRAWINGS

Example embodiments are described in detail below with reference to the attached drawing figures, wherein.

DETAILED DESCRIPTION

Figure 1:
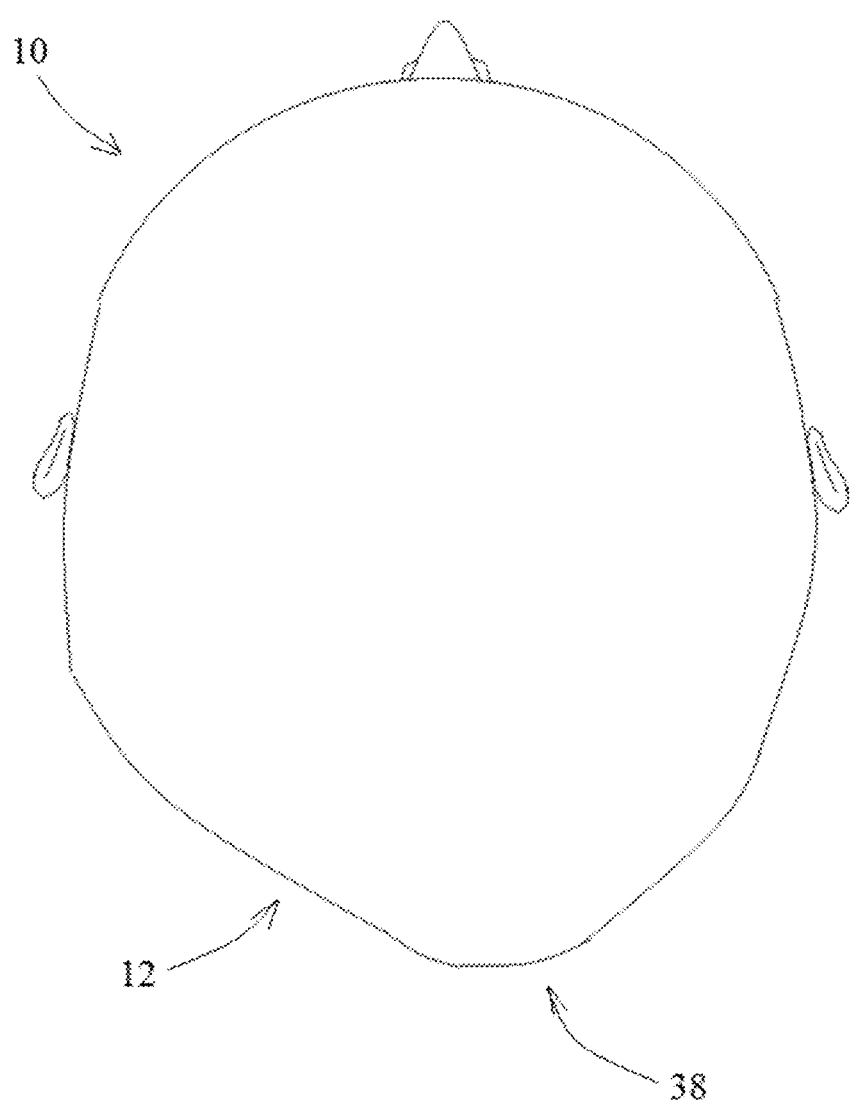
FIG. 1 is a view of a baby's head.

Example embodiments will now be described more fully with reference to the accompanying drawings. Example embodiments are not intended to limit the invention since the invention may be embodied in different forms. Rather, the example embodiments are provided so that this disclosure will be thorough and complete, and will fully convey the scope of the invention to those skilled in the art. In the drawings, the sizes of components may be exaggerated for clarity.

In this application, when an element is referred to as being "on," "attached to," "connected to," or "coupled to" another element, the element may be directly on, directly attached to, directly connected to, or directly coupled to the other element or may be on, attached to, connected to, or coupled to any intervening elements that may be present. However, when an element is referred to as being "directly on," "directly attached to," "directly connected to," or "directly coupled to" another element or layer, there are no intervening elements present. In this application, the term "and/or" includes any and all combinations of one or more of the associated listed items.

In this application, the terms first, second, etc. are used to describe various elements and components. However, these terms are only used to distinguish one element and/or component from another element and/or component. Thus, a first element or component, as discussed below, could be termed a second element or component.

In this application, terms, such as "beneath," "below," "lower," "above," "upper," are used to spatially describe one element or feature's relationship to another element or feature as illustrated in the figures. However, in this application, it is understood that the spatially relative terms are intended to encompass different orientations of the structure. For example, if the structure in the figures is turned over, elements described as "below" or "beneath" other elements would then be oriented "above" the other elements or features. Thus, the term "below" is meant to encompass both an orientation of above and below. The structure may be otherwise oriented (rotated 90 degrees or at other orientations) and the spatially relative descriptors used herein interpreted accordingly.

Example embodiments are illustrated by way of ideal schematic views. However, example embodiments are not intended to be limited by the ideal schematic views since example embodiments may be modified in accordance with manufacturing technologies and/or tolerances.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments relate to a pillow usable for preventing and/or treating plagiocephaly.

Figure 2:
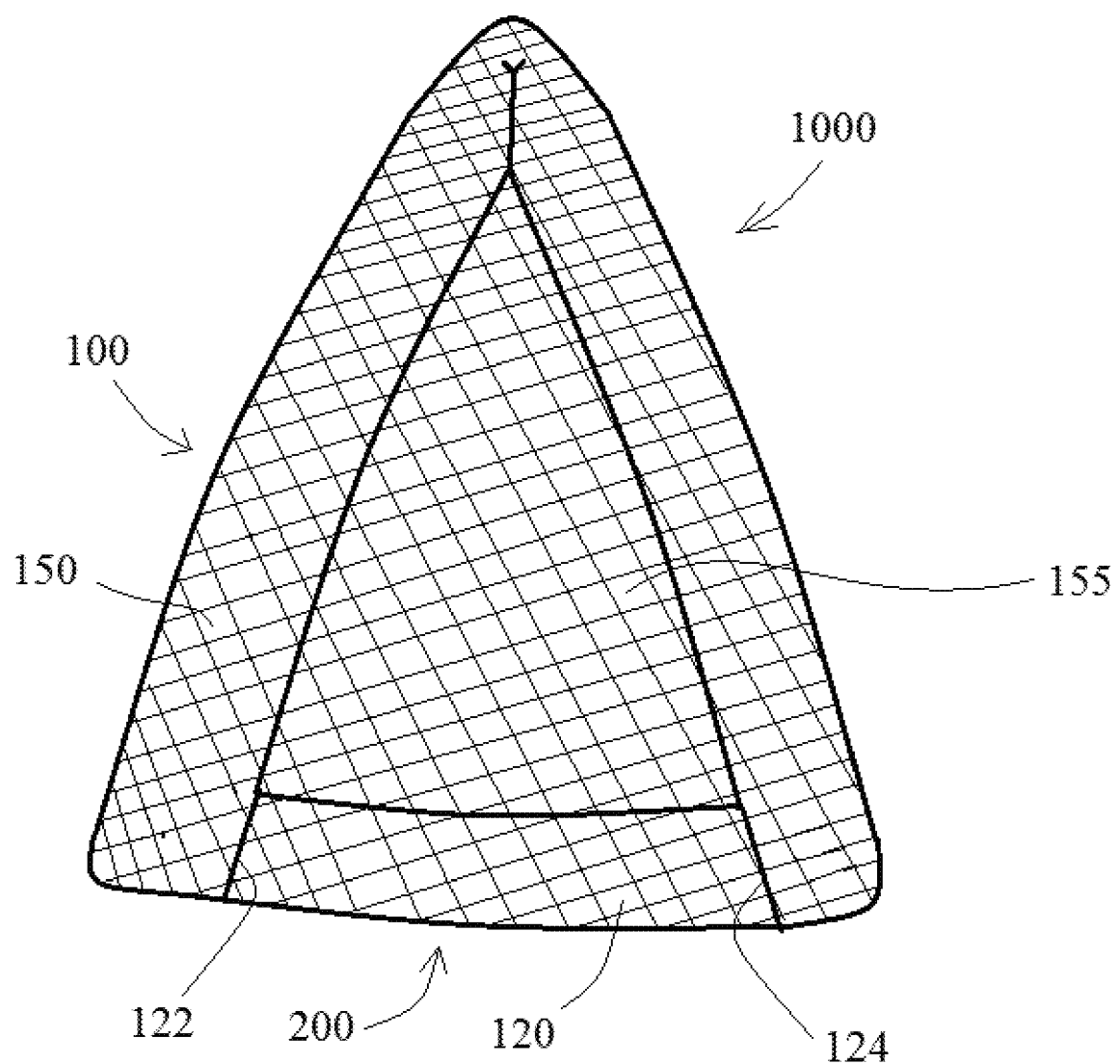
FIG. 2 is a view of a pillow in accordance with example embodiments.

FIG. 2 is a top view of a pillow 1000 usable to prevent and/or treat plagiocephaly in infants and small children. As shown in FIG. 2, the pillow 1000 may be comprised of a body 100 and a cover 200 on or enclosing the body 100. In the nonlimiting example of FIG. 2, the body 100 has a neck support 120 and at least one arm 150 extending from a first end 122 of the neck support 120 to a second end 124 of the neck support 120. The at least one arm 150 may be formed to create void 155 into which an infant's head may be placed. As shown in the nonlimiting example of FIG. 2, the void 155 may be covered by the cover 200.

In one arrangement, body 100, which may include neck support 120 and/or arm 150, may be formed of a hollow member or have a continuous hollow chamber or a plurality of hollow chambers at its middle. This hollow arrangement may provide some added comfort as the hollow chamber allows the main body 100 to deform under the pressure of the baby's head. This hollow chamber may also provide less force upon the baby's head as the hollow interior allows for additional flexing and compression of body 100. In an alternative arrangement, these components are formed of a solid material and does not include a hollow chamber or hollow interior. In addition, the durometer or hardness/softness of the material that forms body 100 is a variable that may be adjusted depending on the desired result and effects. That is, the durometer of body 100 may be adjusted to provide a softer or harder body 100. The durometer of the body 100 may be consistent throughout the body 100, or alternatively the durometer of the body 100 may vary across or through the body 100, such as having a harder core while having a softer exterior, or having a softer top side and a harder bottom side, or the like. Body 100 may be formed of open cell foam, closed cell foam, memory foam (often referred to as "viscoelastic" polyurethane foam, or low-resilience polyurethane foam (LRPu)), or the like materials.

In another embodiment, the at least one arm 150 may resemble a bladder configured to hold a fluid such as air or water. An advantage of this embodiment is that a stiffness of the at least one arm 150 may be controlled by controlling the volume or pressure of fluid in the at least one arm 150. For example, if a relatively stiff arm 150 is desired the pressure within the arm 150 may be maintained relatively high. If a relatively flexible arm 150 is desired a relatively low pressure may be maintained in the at least one arm 150. Thus, in this nonlimiting example embodiment, a stiffness of the at least one arm 150 may be controlled by controlling a pressure or amount of fluid within the at least one arm 150.

In the nonlimiting example of FIG. 2, the cover 200 may be a porous material, for example, cloth net. Porosity of the material may be important to allow ventilation through the pillow 1000 so that, in the event an infant flipped over on the pillow 1000, the pores would allow for adequate ventilation for the infant. In at least one nonlimiting example embodiment, the cover 200 may be stiff enough to support and apply pressure to a baby's head when the baby's head is placed on the pillow 1000. This may be important in shaping or reshaping a baby's head. In one arrangement, the cover 200 acts as a cradle or hammock that supports the baby's head and allows it to reshape itself without causing specific pressure points. While in the arrangement shown in FIG. 2 the cover 200 extends across the entire pillow 1000, such that the cover 200 spans the hollow interior of pillow 1000, in an alternative arrangement, cover 200 is tubular in shape and fits around the body 100 while not crossing the hollow interior of pillow 1000. Cover 200 may include buttons, snaps, a zipper, a draw string, a hook and loop arrangement (e.g. Velcro®) or any other component that facilitates cover to be placed or fitted over body 100 as well as removed from body 100 so as to allow for removal, washing and replacement. In an alternative arrangement, cover 200 is permanently affixed around and/or to body 100 such as by stitching, gluing, welding, molding or otherwise forming cover 200 around or on or into body 100. In some embodiments a cover 200 is not present and/or in some embodiments cover 200 is an accessory that may be added if desired.

Figure 3:
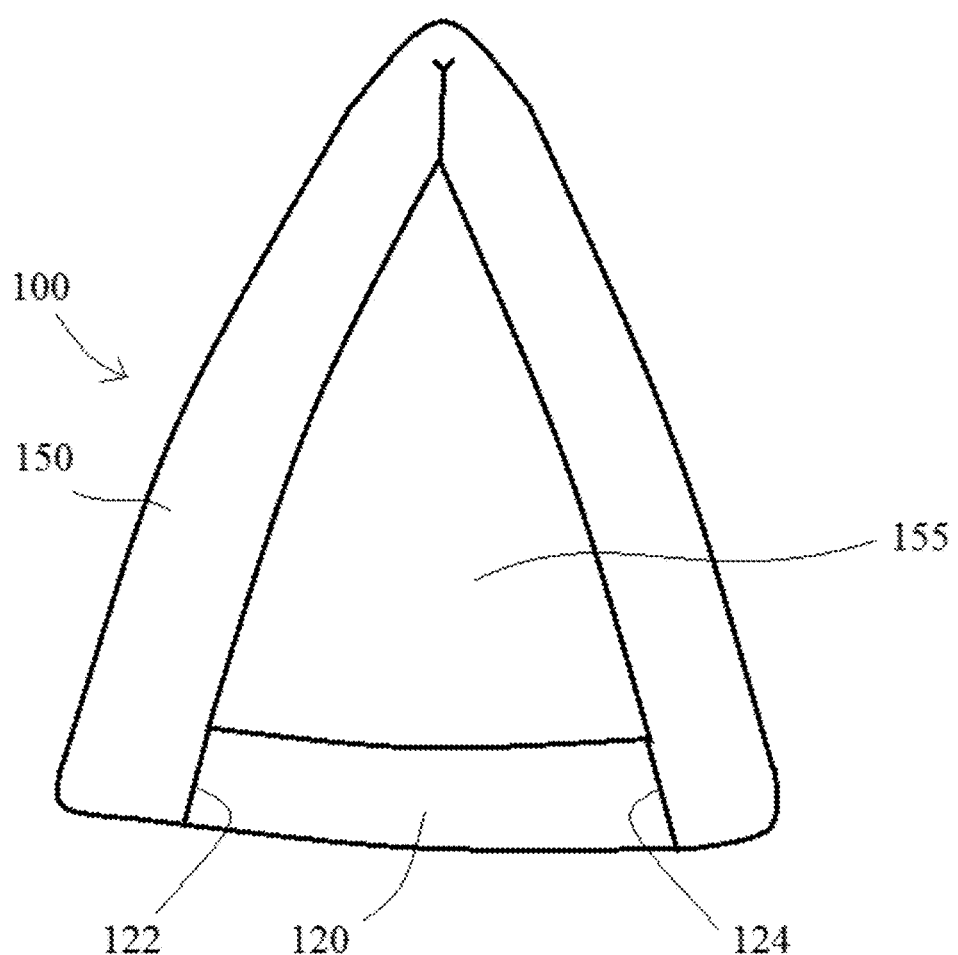
FIG. 3 is a view of a body in accordance with example embodiments.

FIG. 3 illustrates an example of the body 100. As shown in FIG. 3, and explained above, the body 100 may have a neck support 120 and at least one arm 150 extending from the neck support 120. In the nonlimiting example of FIG. 3, the at least one arm 150 may be formed from a foam cylinder 145 (see FIG. 4), for example, an open cell or closed cell foam cylinder. Foam cell materials are relatively light weight, durable, and unlikely to cause injury if grasped by an infant. Other potential materials include, but are not limited to, plastics, silicone, rubber, or rubber-like materials, gel, stuffing, foam beads, or any other compressible or soft material. Notably, manufacturer safety standards require the materials used in products such as that described herein cannot be made of material which a child could, in theory, bite and remove a chunk, thereby causing a choking hazard. As such, while the materials used may be "soft" they will be sufficiently strong and durable so as to prevent tearing. In one arrangement, the "soft" material may be covered with a layer that prevents tearing while still allowing the material to be compressible or "soft".

Figure 4:
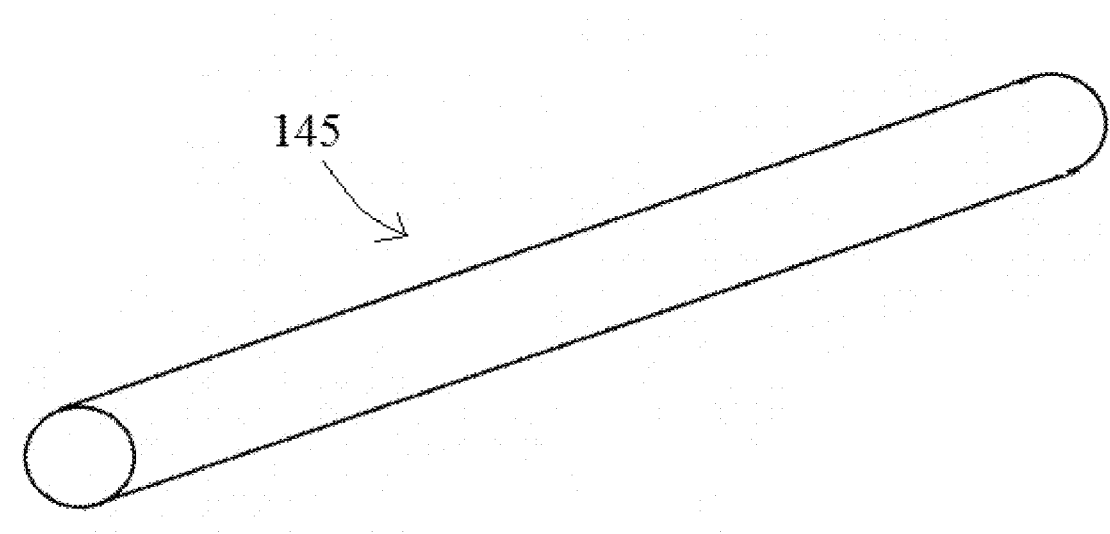
FIG. 4 is view of a cylinder in accordance with example embodiments.

FIG. 4, for example, shows a foam cylinder 145 usable to form the at least one arm 150 of the pillow 1000. As shown in FIG. 4, the foam cylinder 145 may have a circular cross-section which may have a diameter of about 0.75 inches to about 2.5 inches and a length of about 12 to about 20 inches, however any other size, shape and design is hereby contemplated for use. In one particular nonlimiting example embodiment, a diameter of about 1.5 inches and a length of about 16 inches, that is bent at its approximate middle to form a triangle with neck support 120, functioned particularly well as an arm in a pillow used to treat plagiocephaly.

Figure 5:
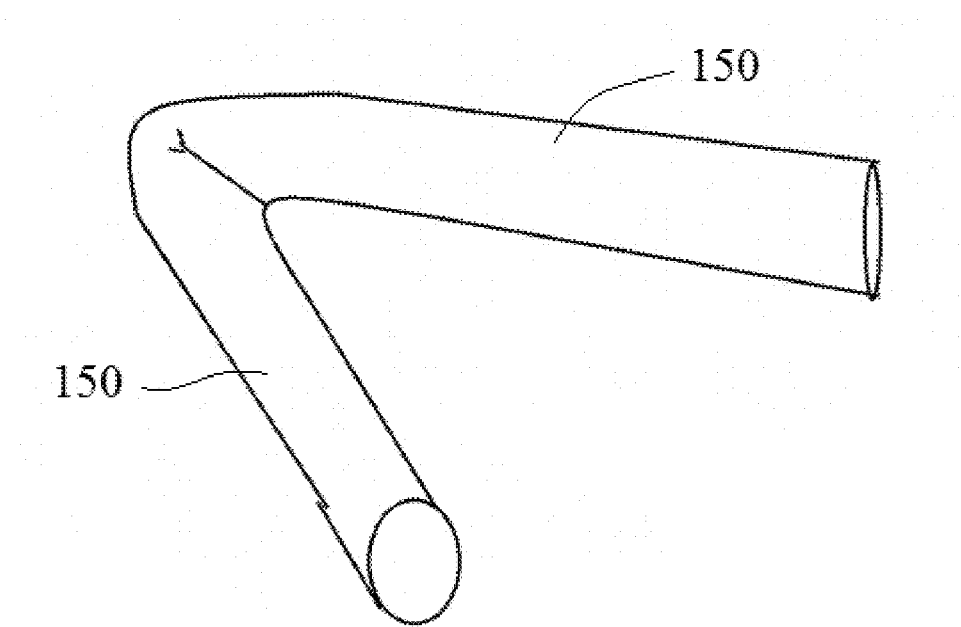
FIG. 5 is a view of the cylinder bent to form at least one arm in accordance with example embodiments.

As shown in FIG. 5, the foam cylinder 145 may be bent to form an angled foam structure which may be used to form the at least one arm 150 extending from the neck support 120. It is understood that a foam cylinder having a circular cross-section is provided only for purposes of illustration. For example, rather than having a circular cross-section, the foam cylinder may have a polygonal (for example, square or rectangular or triangular or octagonal or any other shape) cross-section, or the surface may be curved or sloped toward the open center of the pillow 1000.

Figure 6:
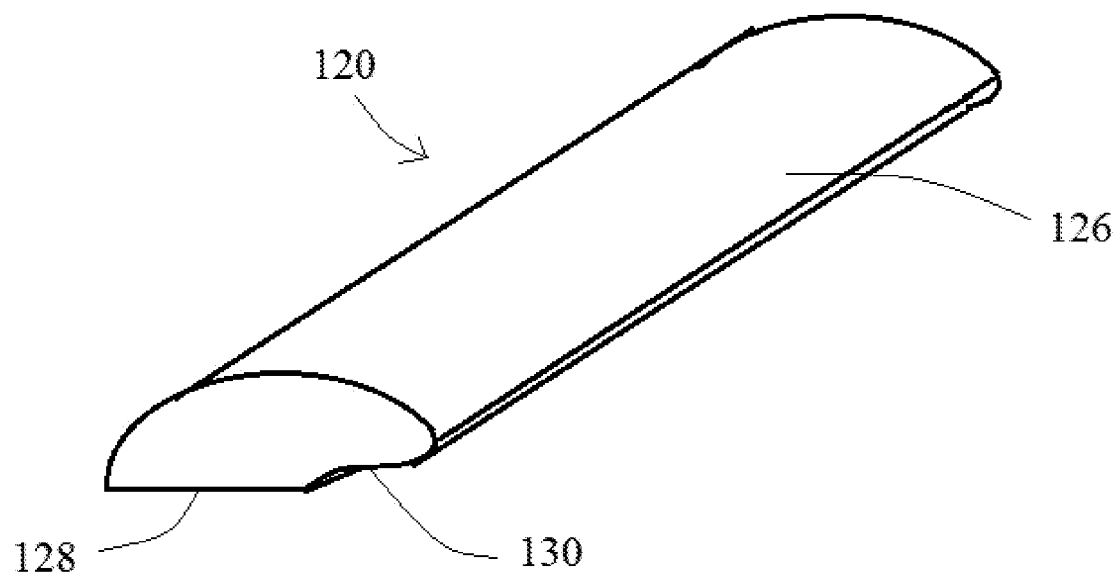
FIG. 6 is a view of a neck rest in accordance with example embodiments.
Figure 7:
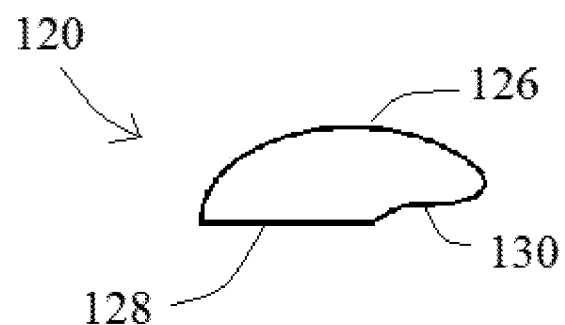
FIG. 7 is a cross-section view of a neck rest in accordance with example embodiments.

In example embodiments, the neck support 120, may also be formed from a foam material. FIG. 6, for example, illustrates an example of a foam material which may be used to form the neck rest 120. FIG. 7 illustrates a cross-section of the neck support 120. As shown in FIGS. 6 and 7, an upper surface 126 of the neck support 120 may be arcuate to help distribute the weight of an infant's neck while the infant is placed on the pillow 1000. A lower surface 128 of the neck support 120 may be, but is not required to be, flat. This may help distribute a loading from the baby's neck to a flat surface, for example, a mattress or a car seat, which may improve the pressure distribution to the baby's neck. A flat lower surface 128 may also help maintain the pillow 1000 in an upright position and prevent it from flipping over. Also, a non-slip or gripping surface, coating or component may be provided on the lower surface 128 to prevent movement of the pillow 1000. Though not required, an arcuate surface 130 extending from the lower surface 128 to the upper surface 126 may be provided.

Figure 8:
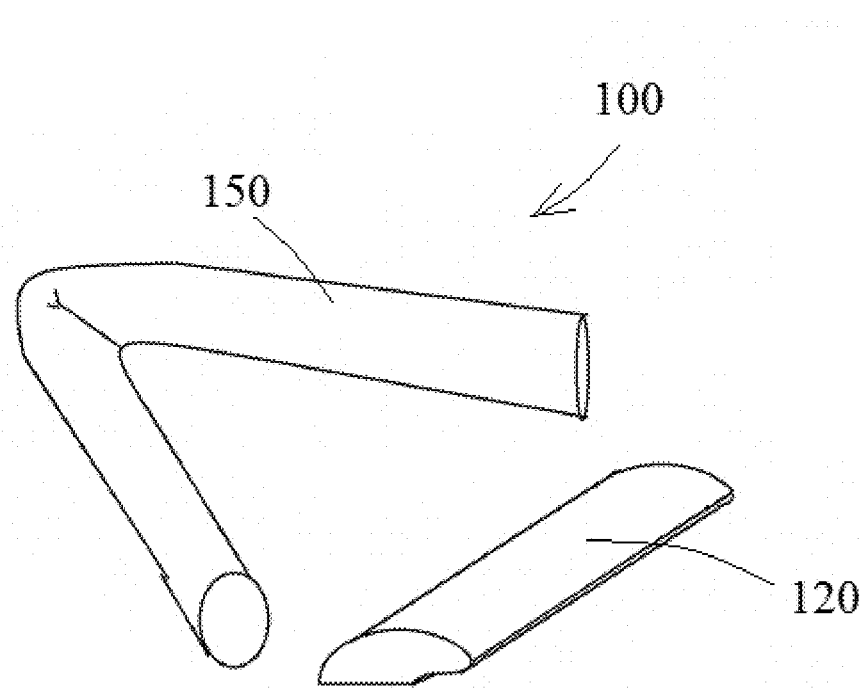
FIG. 8 is an exploded view of a body in accordance with example embodiments.
Figure 9:
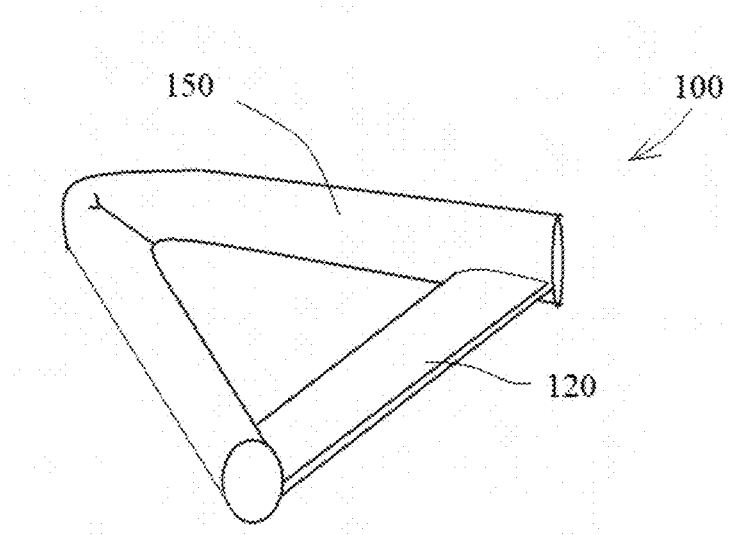
FIG. 9 is as view of a body in accordance with example embodiments.

FIG. 8 illustrates an exploded view of the body 100 in accordance with example embodiments and FIG. 9 illustrates the body 100 in an assembled state. As shown in FIGS. 8 and 9 the at least one arm 150 may be formed separately from the neck rest 120 and then attached to one another to form the completed body 100 shown in FIG. 9. For example, a first end of the at least one arm 150 may be attached to a first end 122 of the neck rest 120 and a second end of the at least one arm 150 may be attached to the second end 124 of the neck rest 120. The at least one arm 150 may be connected to the neck rest 120 by any number of means including, but not limited to, using adhesives and/or tapes. In an alternative arrangement the body 100 of pillow 1000 is formed as a single solitary, unitary and monolithic part through a molding or forming process. This arrangement provides a durable body 100 that does not require assembly or other manufacturing steps.

Figure 10:
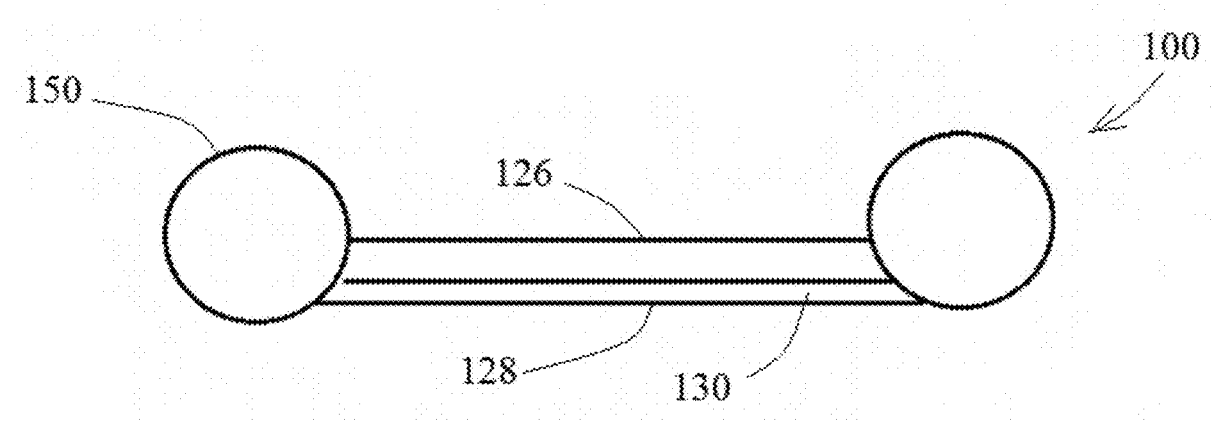
FIG. 10 is an end view of a body in accordance with example embodiments.
Figure 11:
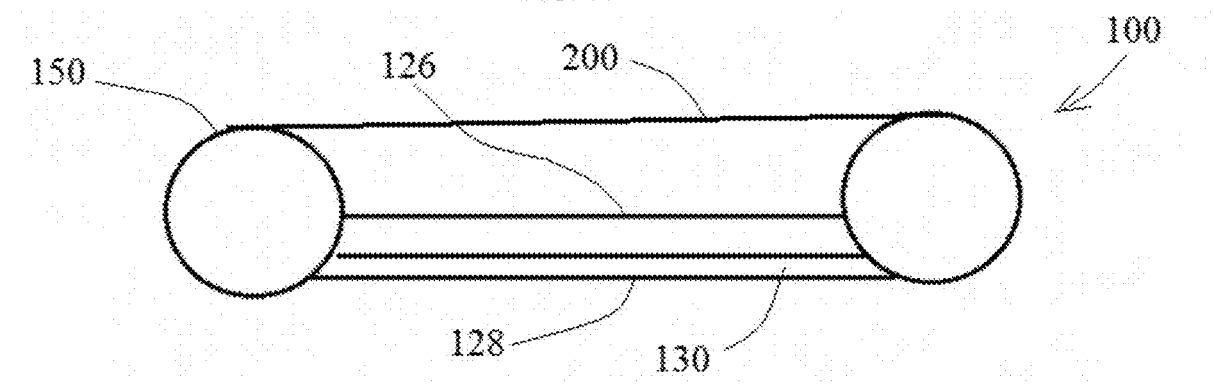
FIG. 11 is an end view of a pillow in accordance with example embodiments.

FIG. 10 illustrates an end view of the body 100. As shown in FIG. 10, the upper surface 126 of the neck rest 120 may be below the upper most portions of the at least one arm 150. This may prevent a baby's head from rotating back too far back. FIG. 11 illustrates the body 100 covered by the cover 200.

Figure 12:
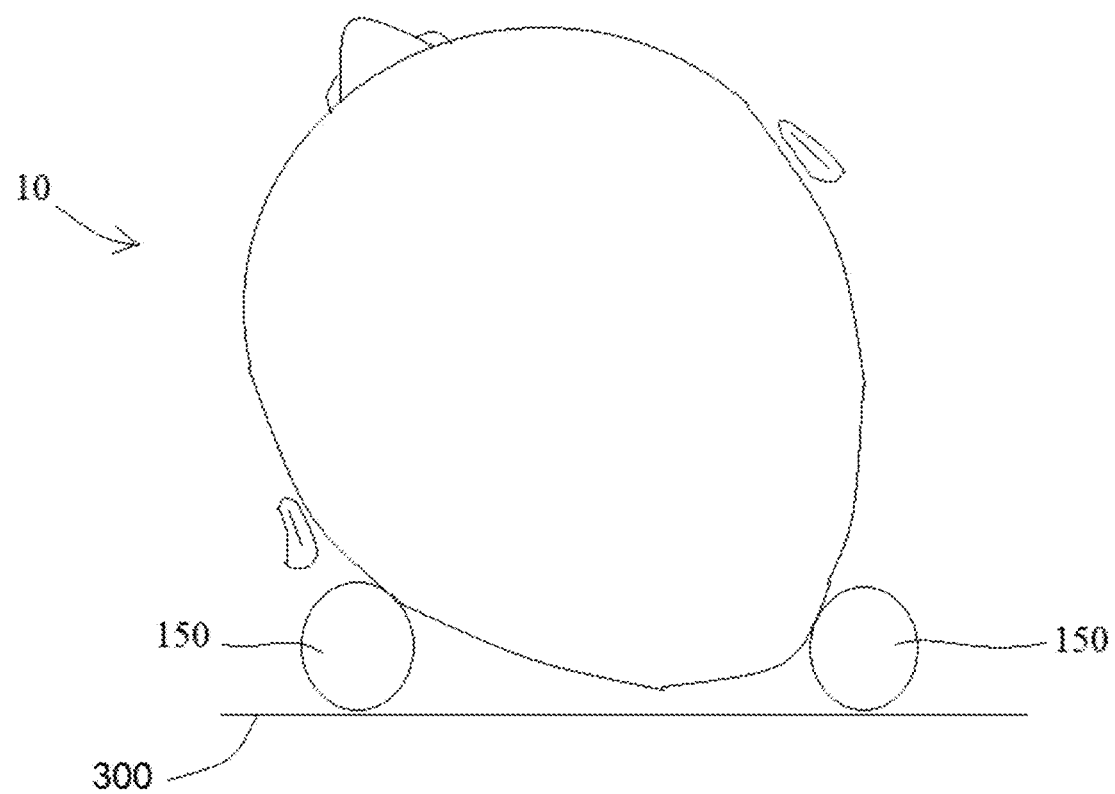
FIG. 12 is a view of a baby's head supported by the arms of a pillow in accordance with example embodiments.

FIG. 12 illustrates a baby's head 10 supported by pillow 1000 in accordance with example embodiments. As shown in FIG. 12, the baby's head 10 is supported in at least two spots and off of the support surface 300 the pillow 1000 is laid. This reduces localized forces a baby's head normally experiences when laid on a flat surface and thereby reduces localized stresses in a baby's skull when laid in the pillow 1000 in accordance with example embodiments. This is because the baby's skull is supported in two spots rather than one as would be the case if the baby was laid on a flat surface. In addition, some children with plagiocephaly have a skull with a center of gravity shifted away from the flat spot and towards the protruding portion of the child's head 10. In the pillow 1000 of example embodiments, the portion of the pillow 1000 associated with the child's protrusion generally experiences a slightly higher force than the portion of the pillow 1000 associated with the flat spot. As a consequence, the bones in the skull forming the protrusion are encouraged to flatten out and the bones of the skull associated with the flat portion are encouraged to grow outward until the skull forms a substantially symmetrical shape. As such, not only is the pillow 1000 capable of reducing localized stresses on a baby's head but, in some cases, the stresses actually encourage a baby's skull grow in a symmetrical fashion thereby reducing a baby's tendency to form plagiocephaly.

Figure 34:
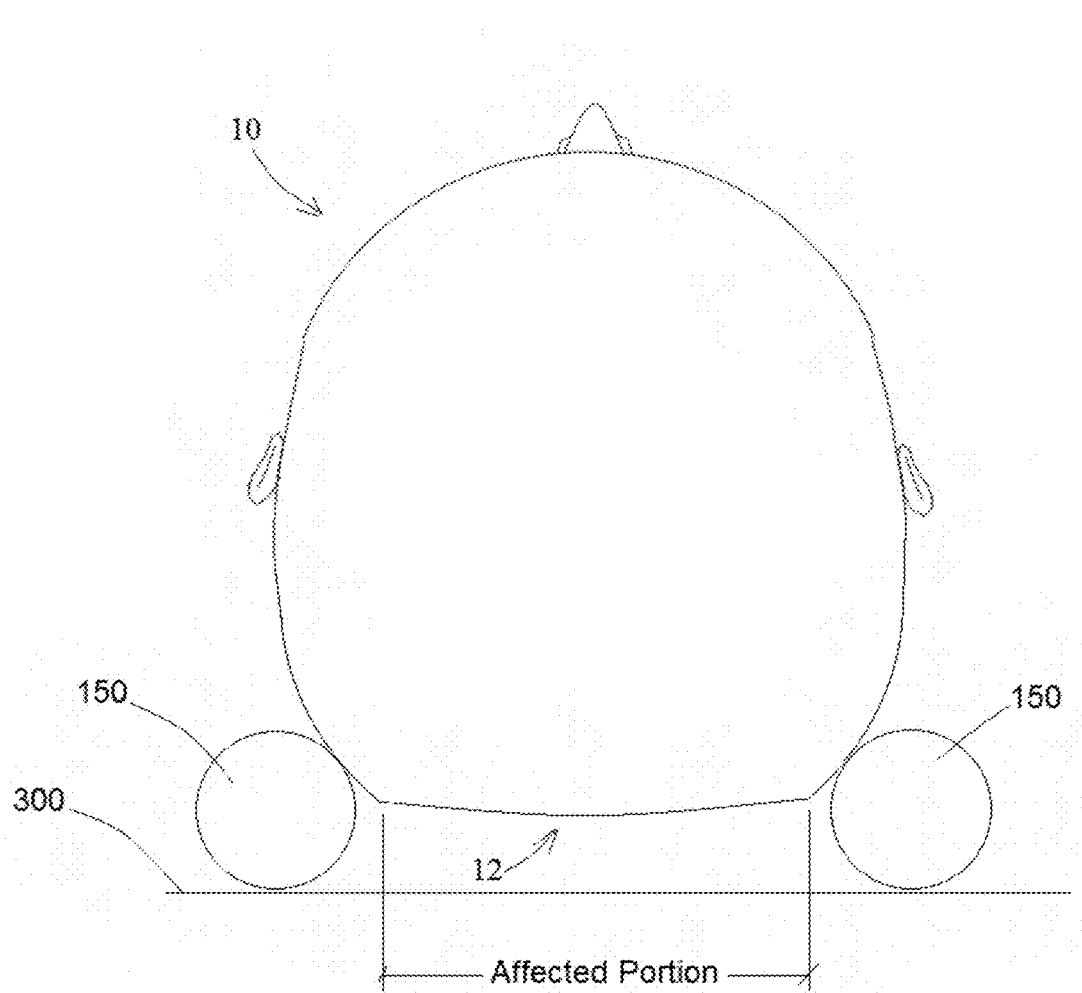
FIG. 34 is a view of a baby's head supported by a pillow in accordance with example embodiments.

FIG. 34 illustrates a baby's head 10 supported by pillow 1000 in accordance with example embodiments. As shown in FIG. 34, the baby's head 10 is supported in at least two spots and off of the support surface 300 the pillow 1000 is laid. In this example embodiment the baby's head 10 includes a flat spot 12, an example of an affected portion of the head 10. The remainder of the head 10 is relatively normal and may be construed as an unaffected portion of the head 10. In this nonlimiting example embodiment, the pillow 1000 has an open center 155 and is placed on a resting surface 300, for example, a bed, a floor, or a car seat. As shown in FIG. 34, the baby's head is placed on the pillow 1000 in such a manner that the unaffected portion of the head engages and is supported by the at least one arm 150 of the pillow 1000 so that the affected portion 12 of the head 10 is raised above the resting surface 300 thereby allowing the affected portion 12 of the head 10 to naturally reform without interference by the resting surface. As on skilled in the art would readily appreciate, supporting a baby's head 10 in the manner described above reduces localized forces a baby's head normally experiences when laid on a flat surface. This is because the baby's skull is supported in two spots rather than one as would be the case if the baby was laid on a flat surface.

It is understood that the pillow 1000 having the at least one arm 150 and neck support 120 may be considered a pillow having a hole 155 therein. It is also understood that the at least one arm 150 and neck support 120 may be considered a frame. A characteristic of the frame is that it must be hard enough to support a head 10 of an infant in a levitated state thereby allowing the head to naturally reform and fix a flat spot 12. In example embodiments the pillow 1000 may not include any structure that contacts, or offers any serious resistance to, the flat spot/affected portion 12 of the head 10. This allows the affected portion 12 to reform naturally. In the arrangement shown there is an air space below the affected portion 12 and the support surface 300. That is, there is no structure between the back of affected portion 12 of the baby's head 10 and the surface 300 supporting the pillow 1000. In another arrangement a soft netting or cover may be between the surface supporting the pillow 1000 and the affected portion 12 of the baby's head 10 which cradles the affected portion 12 of the baby's head 10. However, in this latter embodiment, the soft netting or cover must be compliant enough to allow the affected portion 12 of the baby's head 10 to reform. The netting or cover may span the open interior of the pillow and may have a natural tendency to cradle the head 10 including the affected portion 12 which may help reform the affected portion 12 to a more rounded configuration rather than a flat one.

Figure 13:
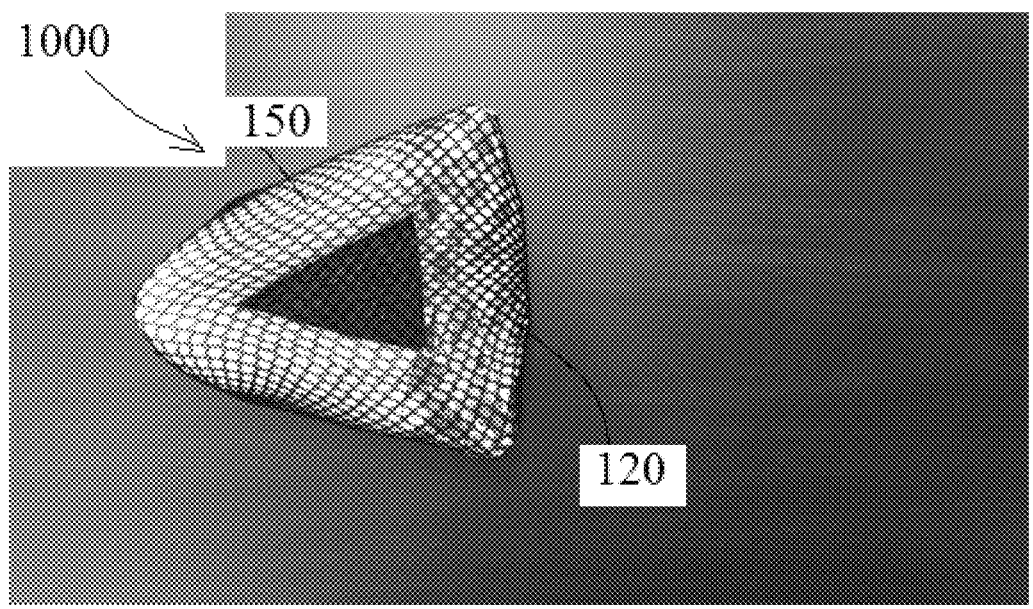
FIG. 13 is a view of a pillow on a flat surface in accordance with example embodiments.
Figure 14:
FIG. 14 is a view of a baby on the pillow in accordance with example embodiments.

FIGS. 13 and 14 illustrate an example of how the pillow 1000 in accordance with a nonlimiting example embodiment may be used. As shown in FIG. 13 the pillow 1000 may be positioned on a flat surface, for example, a table, a bed, or even a car seat. As shown in FIG. 14, a baby's head 10 may be placed on the pillow so the baby's neck is supported by the neck support 120 and the baby's skull is supported by the at least one arm 150.

Figure 15:
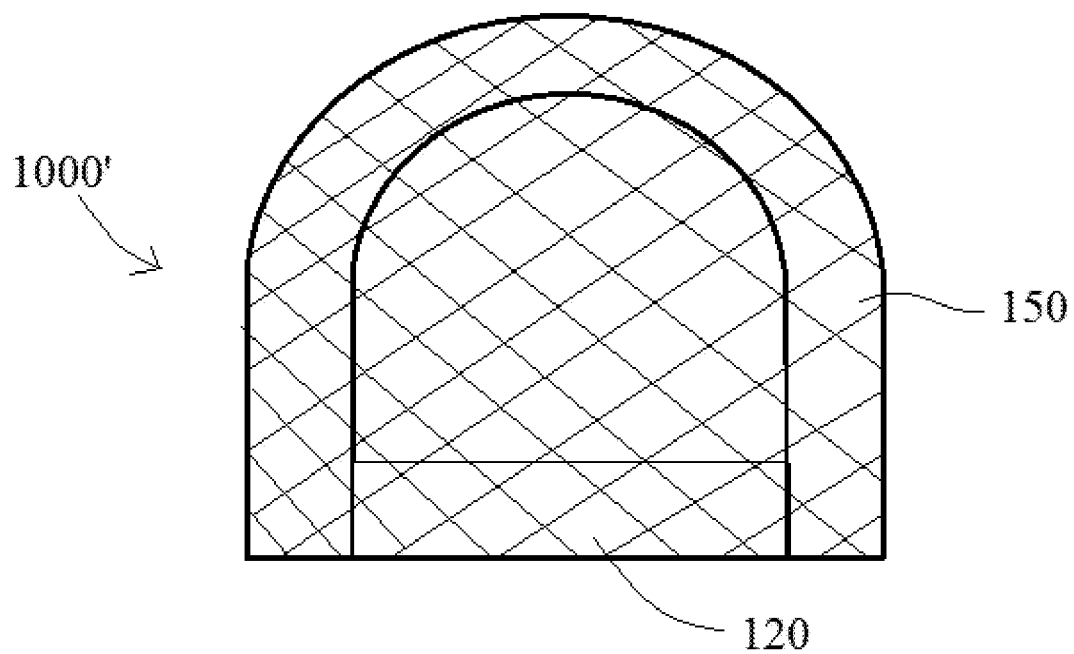
FIG. 15 is a view of another pillow in accordance with example embodiments.
Figure 16:
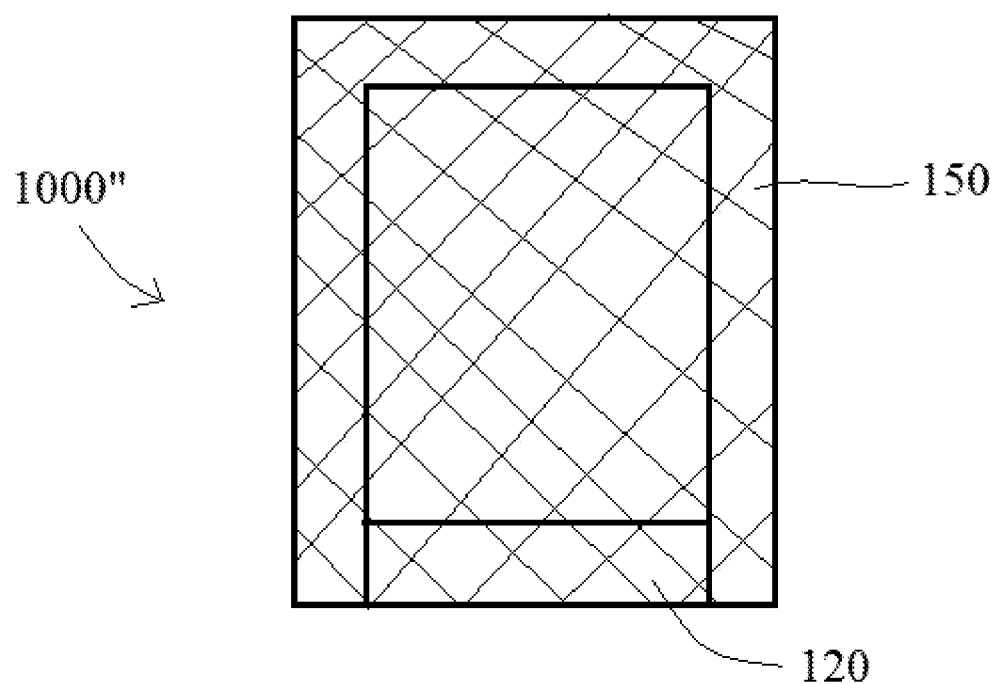
FIG. 16 is a view of another pillow in accordance with example embodiments.

The embodiments of FIGS. 2-14 are not intended to be a limiting disclosure. For example, in FIGS. 2-14 the body 100 is illustrated as having a triangular shape. However, the shape may vary from one embodiment to another. For example, FIG. 15 illustrates another pillow 1000' where the at least one arm 150 has been formed into a semicircular shape rather than an angled or triangular shape. FIG. 16, as another example of a pillow 1000'', illustrates the at least one arm 150 as being formed into a U-shape. In short, there are many ways the inventive concepts described herein may be enabled.

It is also understood that while the body 100 illustrated in FIGS. 2-11 has been described as first foam member connected to a second foam member, the body 100 may actually be formed as a single structure having substantially all of the features of the body 100 illustrated in FIGS. 2-11. For example, the body 100, rather than being formed of two members connected together, may actually be part of a unitary structure formed through a casting, molding or other forming process. Other modifications may include forming the at least one arm 150 and/or the neck rest out of a material, for example, plastic, and then covering the material with a soft material, for example, foam.

In one arrangement, the neck support 120 is low enough for an infant to comfortably rest on the pillow 1000 without obscuring their neck/spine when in supine position. In one arrangement, the upper portion of the pillow 1000 should be at a higher elevation than the upper portion of the neck support 120 to allow the infant's head to remain in a raised position with no pressure on the flat portion of their head. The shape of the pillow 1000 and size and shape of the hole at its middle make it unique to other pillows on the market. A key to treating plagiocepahly is keeping pressure off of the flat spot of the infant's head. The pillows 1000 presented herein are the only presently available product that allows an infant to keep the pressure off of the flat spot of their head. Furthermore, the pillow 1000 is be constructed out of materials that will render it waterproof, so that a child can rest on the pillow during bath time, ultimately allowing a parent to keep a child off of the flat spot on his or her head 100% of the time the child is in supine position.

Alternative Arrangements:

In the arrangement shown in FIGS. 2-14, pillow 1000, when viewed from above or below, is formed in a generally triangular shaped manner, with neck support 120 forming the base of the triangle and the arm 150 forming the other sides of the triangle. However, any other shape is hereby contemplated for use as pillow 1000.

Figure 17:
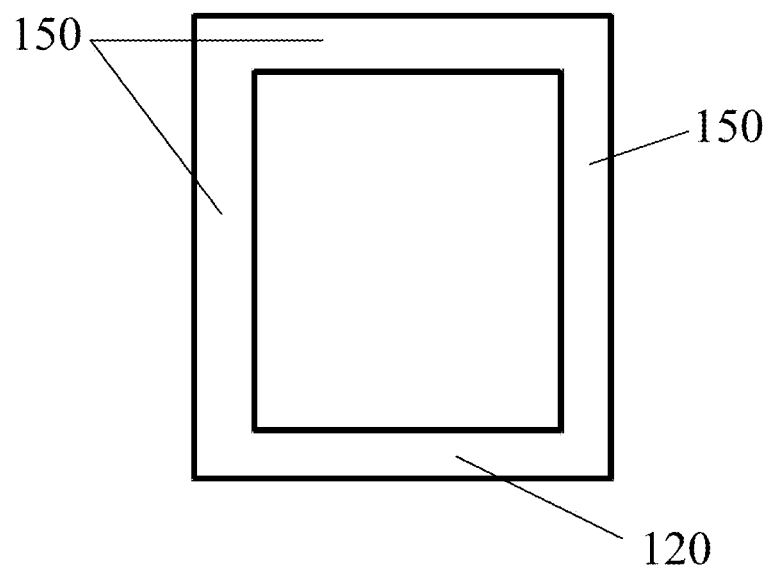
FIGS. 17-27 are elevations views of pillows of various shapes and configurations.

Square or Rectangular:

With reference to FIG. 17, in one arrangement, the combination of the neck support 120 and arm 150 may form a square shape or rectangular shape. In this arrangement, one of the sides of the square or rectangle is formed of neck support 120 and the other sides are formed of arms 150 such that the neck support 120 extends perpendicular under the baby's neck while the sides of the square or body 100 extend parallel to the length of the baby's neck. This is shown, as one example, in FIG. 18 which shows a top view of a square or rectangular body 100 wherein the neck support 120 forms the lower portion of the body 100 and the arm 150 forms the other lengths of the square or rectangular body 100.

Figure 18:
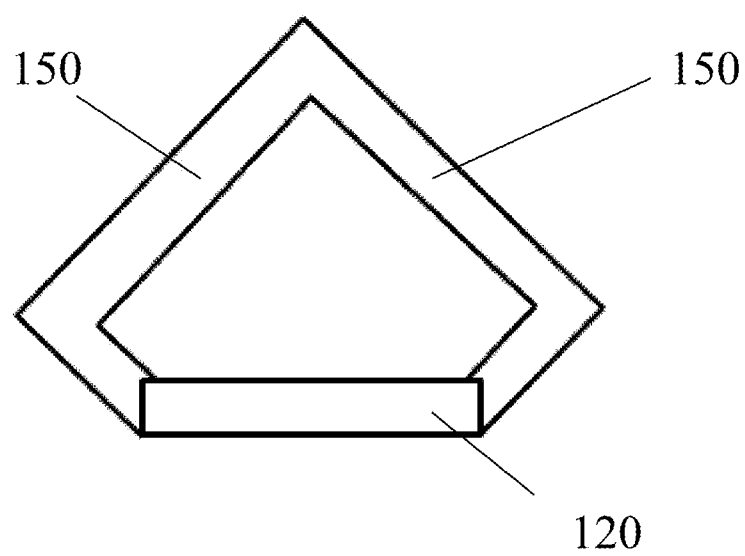

With reference to FIG. 18, in an alternative arrangement, the combination of the neck support 120 and arm 150 may form a square shape or rectangular shape that is configured to be positioned diagonally to the length of the baby's neck. In this arrangement, neck support 120 extends across the bottom of two sides of the square or rectangular shape such that the neck support 120 extends perpendicular to the length of the baby's neck, while the sides of the square or rectangular shaped main body 100 extend at an angle to the sides of the baby's head and/or at an angle to the length of the baby's neck.

Figure 19:
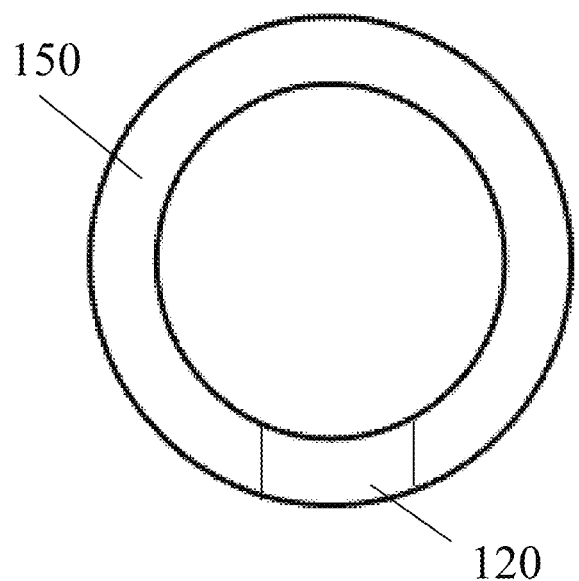

Round:

With reference to FIG. 19, in one arrangement, the combination of the neck support 120 and arm 150 may form a round or curved pillow 1000. In this arrangement, the arm 150 extends around in a curved or circular shape with a portion of the circular shape being formed of the neck support 120. It is this portion of the circular shaped main body 100, the neck support 120, that is positioned under the baby's neck. When in this position, while the neck support 120 is shown as curved, that the neck support 120 essentially extends perpendicular under the baby's neck while the remaining portion or arm 150 of body 100 extends in a circular or curved manner under the baby's head. This is shown, as one example, in FIG. 19 which shows a top view of a circular or curved body 100 wherein the neck support 120 forms the lower portion of the body 100 and the arm 150 forms the other lengths of the circular or curved body 100.

Figure 20:
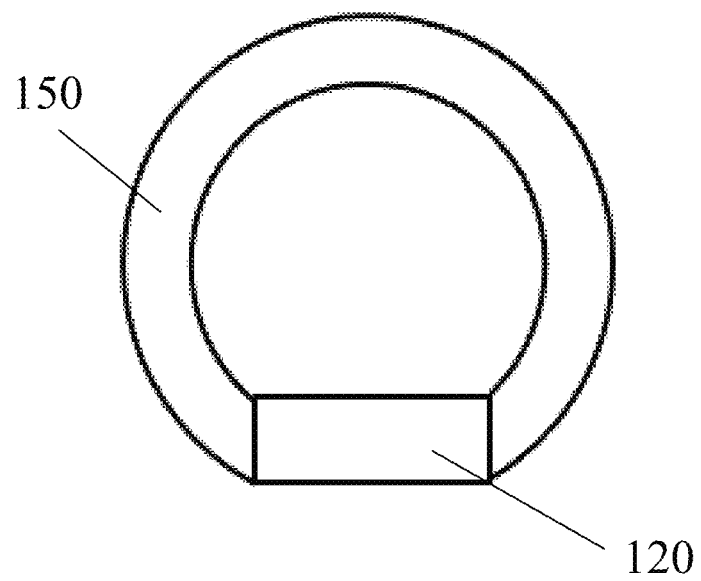

With reference to FIG. 20, in an alternative arrangement, the body 100 takes the form of a round or circular or other curved shape like that shown in FIG. 19, however in this arrangement, the neck support 120, instead of curving in a continuous manner with the reset of the main body 100, the neck support 120 extends across the bottom of two ends of the curved main body 100. In this way, neck support 120 ends the continuous curve of the arm 150. When in position under the baby's neck and head, the straight neck support 120 extends under the baby's neck in a perpendicular manner to the length of the baby's neck while the arm 150 extends around in a curved manner under the baby's head.

Figure 21:
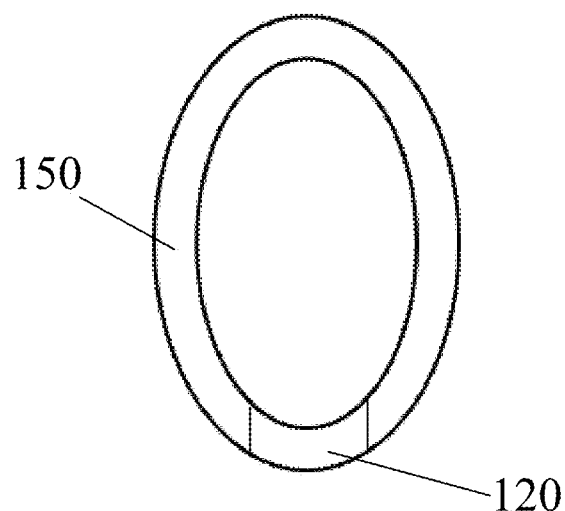

Oval:

With reference to FIG. 21, in one arrangement, the combination of the neck support 120 and arm 150 may form an oval or elliptical pillow 1000. In this arrangement, the arm 150 extends around in a curved or oval shape with a portion of the oval shape being formed of the neck support 120. It is this portion of the oval shaped main body 100, the neck support 120, that is positioned under the baby's neck. When in this position, while the neck support 120 is shown as curved, that the neck support 120 essentially extends perpendicular under the baby's neck while the remaining portion or arm 150 of body 100 extends in an oval or curved manner under the baby's head. This is shown, as one example, in FIG. 21 which shows a top view of an oval or curved body 100 wherein the neck support 120 forms the lower portion of the body 100 and the arm 150 forms the other lengths of the oval or curved body 100.

Figure 22:
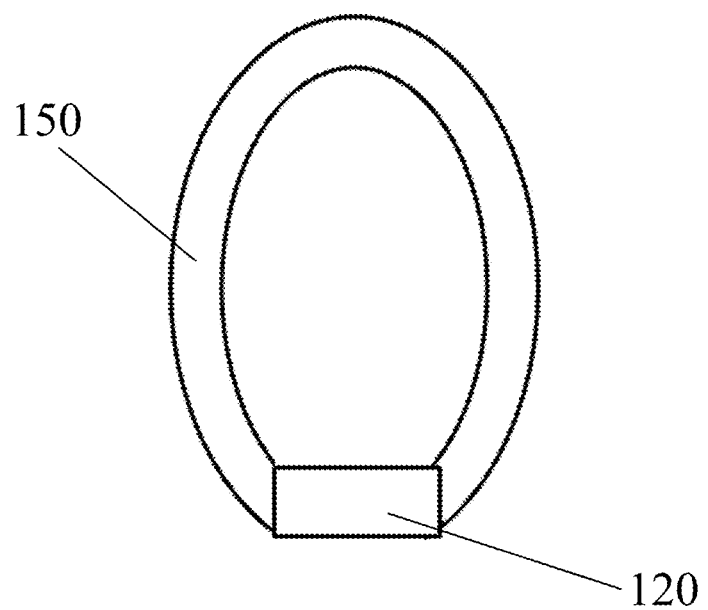

With reference to FIG. 22, in an alternative arrangement, the body 100 takes the form of an oval or other curved shape like that shown in FIG. 21, however in this arrangement, the neck support 120, instead of curving in a continuous manner with the reset of the main body 100, the neck support 120 extends across the bottom of two ends of the oval or curved main body 100. In this way, neck support 120 ends the continuous curve of the arm 150. When in position under the baby's neck and head, the straight neck support 120 extends under the baby's neck in a perpendicular manner to the length of the baby's neck while the arm 150 extends around in a curved manner under the baby's head.

Figure 23:
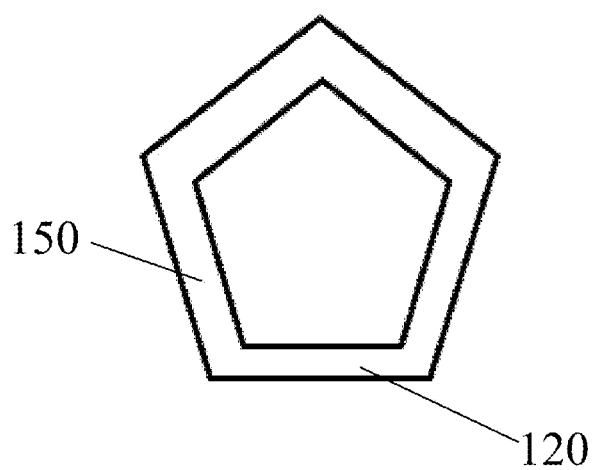

Pentagonal:

With reference to FIG. 23, in one arrangement, the combination of the neck support 120 and arm 150 may form a pentagonal shape, or five sided shape, or other polygonal shape. In this arrangement, one of the sides of the pentagonal shape is formed of neck support 120 and the other sides are formed of arms 150 such that the neck support 120 extends perpendicular under the baby's neck while the sides of the pentagonal body 100 extend around and under the baby's head. This is shown, as one example, in FIG. 23 which shows a top view of a pentagonal body 100 wherein the neck support 120 forms the lower portion of the body 100 and the arm 150 forms the other lengths of the pentagonal body 100.

Figure 24:
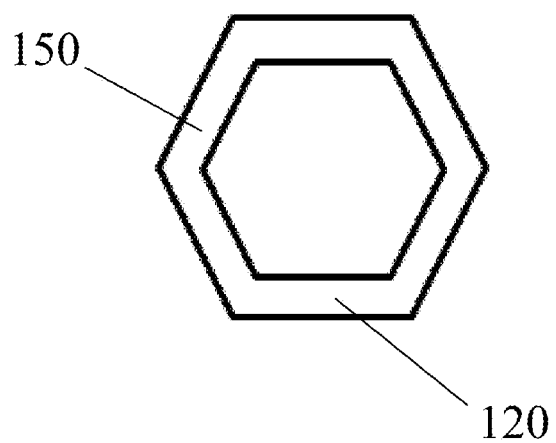

Hexagonal:

With reference to FIG. 24, in one arrangement, the combination of the neck support 120 and arm 150 may form a hexagonal shape, or six sided shape, or other polygonal shape. In this arrangement, one of the sides of the hexagonal shape is formed of neck support 120 and the other sides are formed of arms 150 such that the neck support 120 extends perpendicular under the baby's neck while the sides of the hexagonal body 100 extend around and under the baby's head. This is shown, as one example, in FIG. 24 which shows a top view of a hexagonal body 100 wherein the neck support 120 forms the lower portion of the body 100 and the arm 150 forms the other lengths of the hexagonal body 100.

Figure 25:
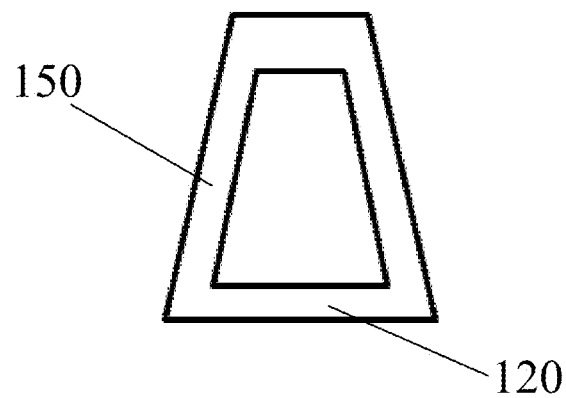

Trapezoidal:

With reference to FIG. 25, in one arrangement, the combination of the neck support 120 and arm 150 may form a trapezoidal shape, or four sided shape with angles other than right angles, where the base and the top are different lengths and two sides are the same or similar lengths or other polygonal shape. In this arrangement, one of the sides of the trapezoidal shape is formed of neck support 120 and the other sides are formed of arms 150 such that the neck support 120 extends perpendicular under the baby's neck while the sides of the trapezoidal body 100 extend around and under the baby's head. This is shown, as one example, in FIG. 25 which shows a top view of a trapezoidal body 100 wherein the neck support 120 forms the lower portion of the body 100 and the arm 150 forms the other lengths of the parallelogram body 100. The pillow 1000 shown in FIG. 25 may be inverted or rotated either way to provide different affects upon the baby's head.

Figure 26:
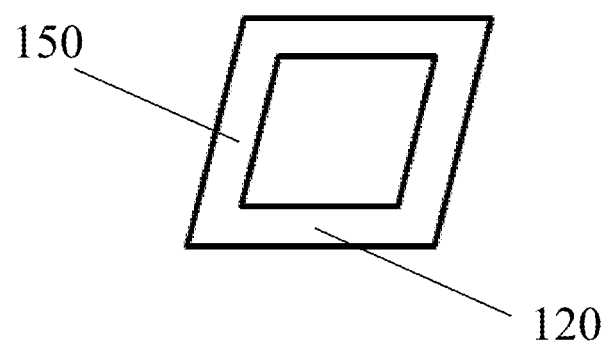
Figure 27:
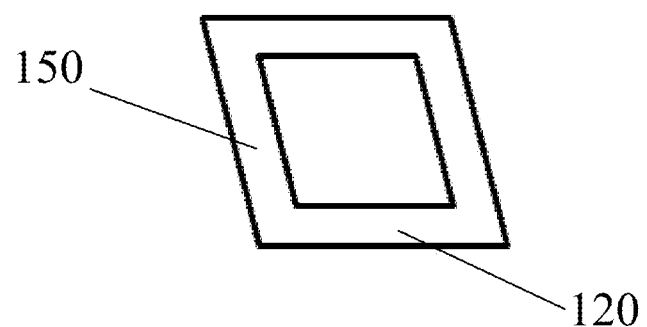

Parallelogram:

With reference to FIGS. 26 and 27, in one arrangement, the combination of the neck support 120 and arm 150 may form a parallelogram shape, or four sided shape with angles other than right angles, or other polygonal shape. In this arrangement, one of the sides of the parallelogram shape is formed of neck support 120 and the other sides are formed of arms 150 such that the neck support 120 extends perpendicular under the baby's neck while the sides of the parallelogram body 100 extend around and under the baby's head. This is shown, as one example, in FIG. 25 which shows a top view of a parallelogram body 100 wherein the neck support 120 forms the lower portion of the body 100 and the arm 150 forms the other lengths of the parallelogram body 100. The pillows 1000 shown in FIGS. 26 and 27 are inverses of one another, that is with the neck support 120 being the lower leg of the parallelogram shape, in FIG. 26 the parallelogram leans right, whereas in FIG. 27 the parallelogram leans left.

Kit of Various Shapes:

While various shapes are shown in use herein, from triangular, square, rectangular, diamond, round, oval, pentagonal, hexagonal, trapezoidal, parallelogram, or any other polygonal shape or other curved shape or the like, it is to be understood that the neck support 120 may be placed at any portion of any of these shapes. Providing pillows 1000 formed of various shapes allows pressure to be applied to different portions of the baby's head and helps correct the flat spot in their skull, or said another way, allows their head to re-form back to a natural shape.

In one arrangement, to facilitate applying pressure to different spots on the baby's head, a pillows 1000 are sold in a kit of a plurality of pillows 1000, each having different sizes and/or shapes. To provide greater variability, these pillows 1000 may have the neck support 120 in different places. That is, as an example, with reference to FIG. 25, the trapezoidal pillow 1000 may provide a different effect on the baby's head by placing the neck support 120 at each different length of the trapezoidal body 100. By providing a plurality of pillows 1000 of different shapes with different lengths of the shapes being the neck support 120, this allows a parent to swap out the pillows 1000 frequently and helps to avoid pressure being applied to the baby's head in the same place day after day. By moving the points of contact around on the baby's head this allows the baby's skull to re-form back to round.

Other Uses:

While pillow 1000 may be most-often used in association with a baby sleeping in a crib, countless other uses are hereby contemplated for use. As one example, pillow 1000 may be used in association with a baby in a baby carrier, such as a car seat, stroller, or the like. As another example, pillow 1000 may be used in association with a baby in a baby swing or other device. As another example, in one arrangement, pillow 1000 is formed of waterproof material, which makes it easier to clean the pillow 100 and makes the pillow 1000 extremely durable and wear resistant. By being waterproof, pillow 1000 may be used during bath time. As is shown herein, pillow 100 is endlessly versatile and may be used in any other situation or application desirable. This versatility ultimately allows a parent to keep a child off of the flat spot on his or her head 100% of the time the child is in supine position. This speeds the healing process and by keeping the infant off of their flat spot 100% of the time prevents the possibility of going backwards and reforming or reinforcing the flat spot.

Figure 28:
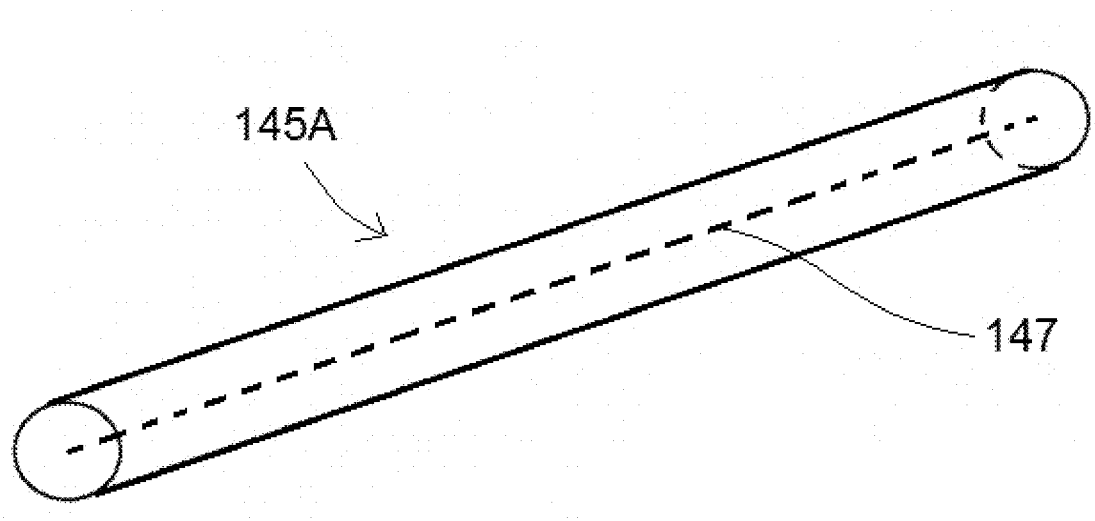
FIG. 28 is a view of a cylinder in accordance with example embodiments.
Figure 29:
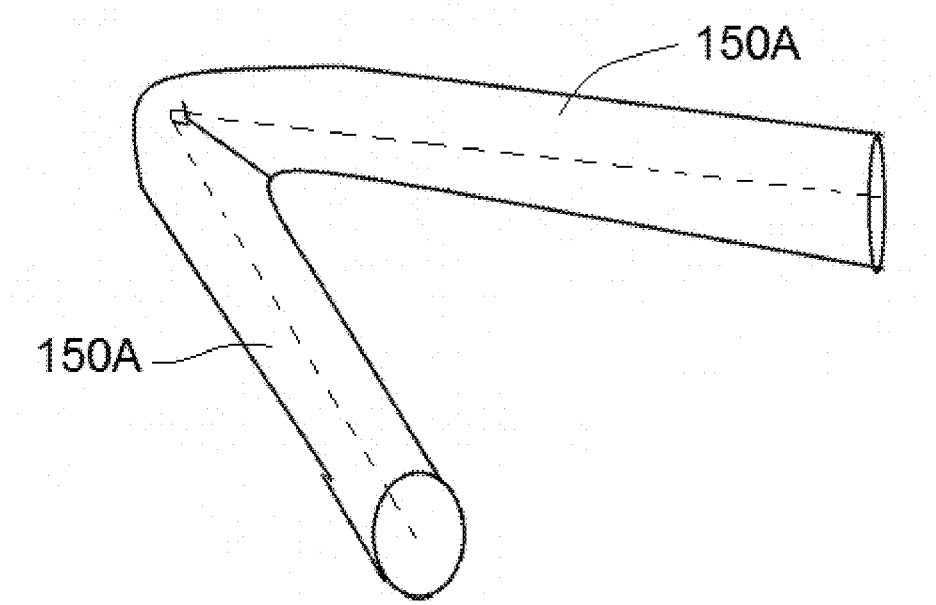
FIG. 29 is a view of the cylinder bent to form at least one arm in accordance with example embodiments.
Figure 30:
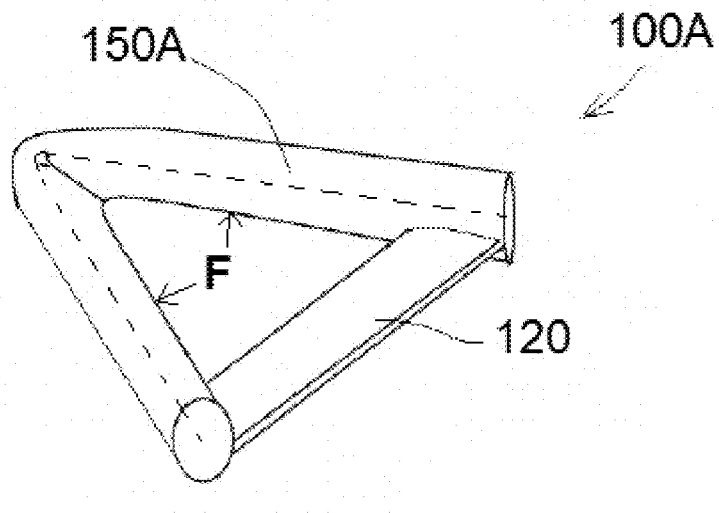
FIG. 30 is a view of a body using the at least one arm in accordance with example embodiments.
Figure 31:
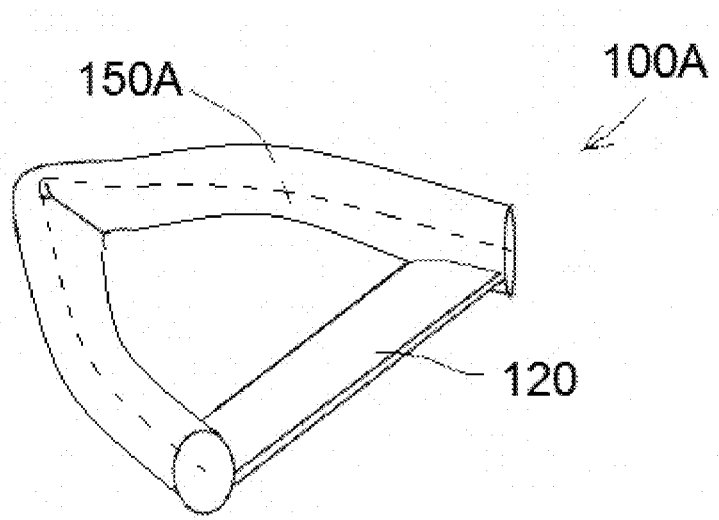
FIG. 31 is a view of the body deformed via the pair of forces.
Figure 32:
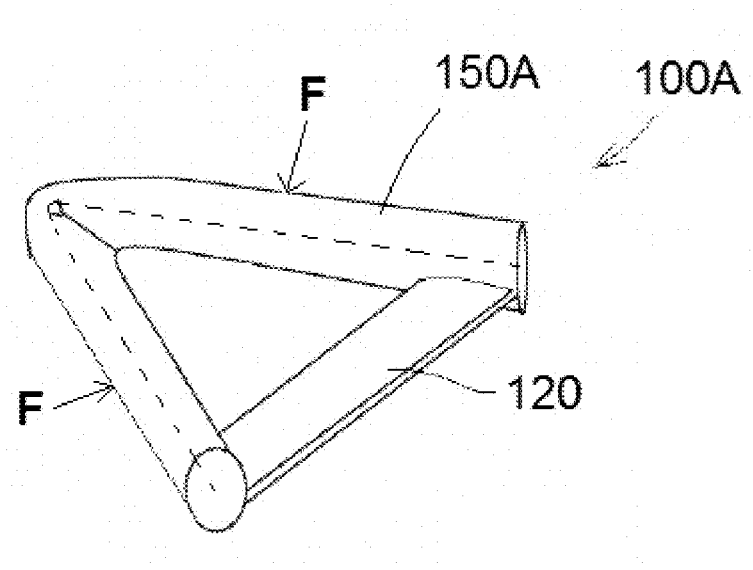
FIG. 32 is a view of the body with another pair of forces applied to deform the at least one arm in accordance with example embodiments.
Figure 33:
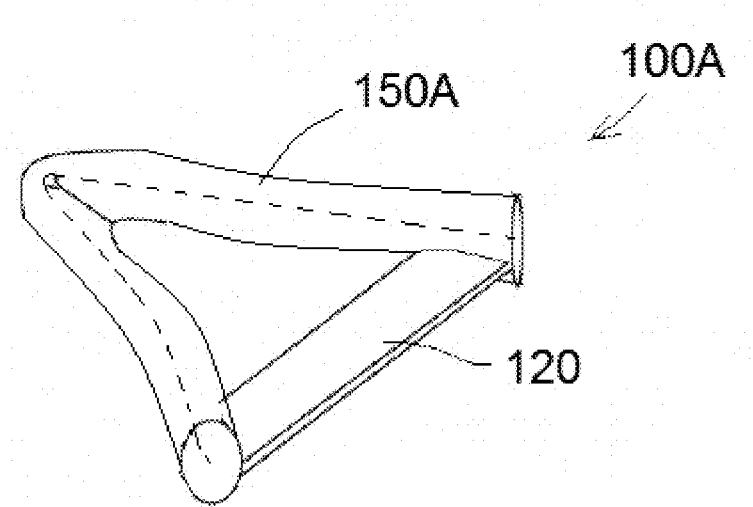
FIG. 33 is a view of the body deformed via the pair of forces.

Example embodiments are not limited by the above. FIG. 28, for example, illustrates a modified cylinder 145A usable to form a body 100A of a pillow, much like cylinder 145 was used to form a body 100 of pillow 1000. In this particular nonlimiting example embodiment the modified cylinder 145A includes a member 147 which may plastically deform under an applied load. The member 147 may, for example, be a wire which may be configured bend under application of a load from a user and retain the bent shape. Surrounding the member 147 is a more compliant material, for example, an open cell foam, a closed cell foam, memory foam (often referred to as "viscoelastic" polyurethane foam, or low-resilience polyurethane foam (LRPu)), or the like. In this example embodiment the modified cylinder 145A may be bent to form a pair of arms 150A similar to the pair of arms 150 of pillow 1000. Like body 100, the pair of arms 150A may attach to a neck rest 120 to form the body 100A as shown in FIG. 30. In this example forces F may be applied to further deform the arms 150A to achieve a desired shape. For example, in FIG. 30 a pair of forces F are applied to an inside surface of the arms 150A to cause the arms 150A to deform outwardly as shown in FIG. 31. Because of the presence of the member 147 the arms 150A may maintain their deformed configuration. As another example, FIG. 32 illustrates the body 100A having a pair of forces F applied to the outside surface of the arms 150A to pinch the arms 150A forcing them to deform inwardly as shown in FIG. 33. Because of the presence of member 147, the arms 150A may maintain the deformed state. The presence of the member 147 allows a user to readily change the shape of the arms 150A to suit the user's particular needs. For example, if the user requires the arms 150A be separated the user can apply a force to the arms to open the body 100 as shown in FIG. 31. On the other hand, if the user requires the arms 150A be closer together, the user may apply forces as shown in FIG. 32 to reduce the distances between the arms 150A. Of course, because of the presence of the member 147 a user could shape the arms 150A to have any shape substantially to those illustrated in FIGS. 15-27.

In one arrangement pillow 1000 and/or arms 150A are formed of a malleable material that may be formed into practically any shape. In this arrangement, no member 147 is needed and instead the material of pillow 1000 and/or arms 150A itself essentially forms member 147. In this arrangement, the material that forms pillow 1000 and/or arms 150A is soft enough to be comfortable for a baby's head, while being sturdy enough to support the baby's head above the resting surface during use, while also having material properties that allow the pillow 1000 and/or arms 150A to be formed into a particular shape while holding that shape during use. In this arrangement, the material that forms pillow 1000 and/or arms 150A is both soft while being rigid, similarly the material that forms pillow 1000 and/or arms 150A is both malleable as well as being rigid enough to hold its shape. Another benefit of this arrangement is that it eliminates the member 147 from poking through the covering material of pillow 1000 and/or arms 150A thereby causing a safety issue.

Example embodiments of the invention have been described in an illustrative manner. It is to be understood that the terminology that has been used is intended to be in the nature of words of description rather than of limitation. Many modifications and variations of example embodiments are possible in light of the above teachings. Therefore, within the scope of the appended claims, the present invention may be practiced otherwise than as specifically described.

I claim:

1. A method of treating plagiocephaly of a baby, comprising: providing a first pillow having at least one arm and a center through hole that is completely surrounded by the first pillow;
    wherein the center through hole of the first pillow extends completely through the first pillow; wherein the baby has a head that has an unaffected portion and an affected portion;
    on a first day:
    placing the first pillow on a resting surface;
    placing the baby on the resting surface adjacent the first pillow; and
    placing the baby's head on the first pillow in such a manner that the unaffected portion of the head engages and is supported by the at least one arm of the first pillow in such a manner that the affected portion of the head is raised above the resting surface thereby allowing the affected portion of the head to naturally reform without interference by the resting surface;
    on a second following day:
    providing a second pillow, distinct from the first pillow, having at least one arm and a center through hole that is completely surrounded by the second pillow;
    wherein the center through hole of the second pillow extends completely through the second pillow;
    wherein the baby has a head that has an unaffected portion and an affected portion;
    placing the second pillow on a resting surface; placing the baby on the resting surface adjacent the second pillow; and
    placing the baby's head on the second pillow in such a manner that the unaffected portion of the head engages and is supported by the at least one arm of the second pillow in such a manner that the affected portion of the head is raised above the resting surface thereby allowing the affected portion of the head to naturally reform without interference by the resting surface;

wherein the first pillow has a first shape configured to contact the head at a first set of contact points;

wherein the second pillow has a second shape different from the first shape and is configured to contact the head at a second set of contact points that are different from the first set of contact points.

2. The method of claim 1, wherein the first pillow includes a neck rest and the at least one arm extends from a first end of the neck rest to a second end of the neck rest.

3. The method of claim 1, wherein placing the baby's head on the first pillow supports the baby's head in at least two locations.

4. The method of claim 1, further comprising:
applying forces to the at least one arm to alter the shape of the at least one arm to have a configuration more conducive to supporting the baby's head.

5. The method of claim 1, further comprising:
applying forces to the at least one arm to alter the shape the at least one arm to have a configuration more conducive to supporting the baby's head, wherein altering the shape of the at least one arm alters the shape of a wire embedded in the at least one arm.

6. The method of claim 1, wherein the center through hole has a triangular shape.

7. The method of claim 1, wherein the at least one arm is comprised of at least one of an open cell foam, a closed cell foam, and a memory foam to provide a soft contact surface for the baby's head.

8. A method of treating plagiocephaly of a baby having a head that has an unaffected portion and an affected portion, comprising:
providing a first pillow having at least one arm and a center through hole that is completely surrounded by the first pillow;
providing a second pillow, distinct from the first pillow, having at least one arm and a center through hole that is completely surrounded by the first pillow;
wherein the center through hole of the first pillow extends completely through the first pillow;
wherein the center through hole of the second pillow extends completely through the second pillow,
the first pillow having a first shape that is configured and arranged to, when the baby's head is placed on the first pillow, contact the baby's head at a first set of contact points and support the baby's head in such a manner that the affected portion of the head is raised above a resting surface;
the second pillow has a second shape that is configured and arranged to, when the baby's head is placed on the second pillow, contact the baby's head at a second set of contact points and support the baby's head in such a manner that the affected portion of the head is raised above the resting surface;
wherein the first set of contact points are at different positions from the second set of contact points;
on a first day:
placing the first pillow on the resting surface;
placing the baby on the resting surface adjacent the pillow;
placing the baby's head on the pillow such that the first set of contact points of the pillow engages the unaffected portion of the baby's head such that the affected portion of the head is raised above the resting surface thereby allowing the affected portion of the head to naturally reform without interference by the resting surface;

on a second following day: placing the second pillow on the resting surface; placing the baby on the resting surface adjacent the pillow; placing the baby's head on the pillow such that the second set of contact points of the pillow engages the unaffected portion of the baby's head such that the affected portion of the head is raised above the resting surface, wherein the second set of contact points are at different positions from the first set of contact points, thereby reducing repetitive contact in the same locations of the baby's head; and on a third following day:
placing the first pillow on the resting surface;
placing the baby on the resting surface adjacent the pillow;
placing the baby's head on the pillow such that the first set of contact points of the pillow engages the unaffected portion of the baby's head such that the affected portion of the head is raised above the resting surface thereby allowing the affected portion of the head to naturally reform without interference by the resting surface.

9. The method of claim 8, wherein the at least one arm includes a first arm and a second arm and the affected portion is arranged between the first arm and the second arm.

10. The method of claim 8, wherein the first pillow includes a neck rest and the at least one arm extends from a first end of the neck rest to a second end of the neck rest.

11. The method of claim 8, wherein placing the baby's head on the first pillow arranges the affected portion of the baby's head between the first set of contact pointes.

12. The method of claim 8, further comprising:
applying forces to the at least one arm to alter the shape the at least one arm to have a configuration more conducive to supporting the baby's head.

13. The method of claim 8, further comprising:
applying forces to the at least one arm to alter the shape the at least one arm to have a configuration more conducive to supporting the baby's head, wherein altering the shape of the at least one arm alters the shape of a wire embedded in the at least one arm.

14. The method of claim 8, wherein the center through hole has a triangular shape.

15. The method of claim 8, wherein the at least one arm is comprised of at least one of an open cell foam, a closed cell foam, and a memory foam to provide a soft contact surface for the baby's head.

16. A pillow for treating plagiocephaly, comprising:
a center through hole;
wherein the pillow has a shape of a polygon having sides of a plurality of different lengths;
wherein the polygon completely surrounds the center through hole;
wherein the center through hole extends completely through the pillow;
wherein the pillow is configured and arranged to support a baby's head to treat plagiocephaly,
the pillow has a shape that is configured and arranged to, when the baby's head is placed on the pillow with a first one of the sides used as a neck support, contact the baby's head at a first set of contact points and support the baby's head in such a manner that the affected portion of the head is raised above a resting surface;
the pillow has a shape that is configured and arranged to, when the baby's head is placed on the pillow with a second one of the sides used as a neck support, contact the baby's head at a second set of contact points and support the baby's head in such a manner that the affected portion of the head is raised above a resting surface;

wherein the first set of contact points are at different positions from the second set of contact points, thereby reducing repetitive contact in the same locations of the baby's head when the first one of the sides and the second one of the sides are alternated in use and thereby allowing the affected portion of the head to naturally reform without interference by a resting surface.

17. The pillow of claim 16, wherein the pillow includes a bendable wire embedded in and extending through each of the sides.

18. The pillow of claim 16, wherein the pillow includes a bendable wire embedded in the pillow; wherein the bendable wire has the shape of the polygon.

19. The pillow of claim 16, wherein the sides of the pillow are configured to plastically deform.

20. The pillow of claim 16, wherein the pillow is comprised of at least one of an open cell foam, a closed cell foam, and a memory foam to provide a soft contact surface for the baby's head.

21. The pillow of claim 16, wherein the first set of contact points and the second set of contact points are positioned so no more than one of the first set of contact points can be aligned with any of the second set of contact point at the same time.

22. The pillow of claim 16, wherein the first set of contact point and second set of contact point are included in a plurality of different sets of contact points;

wherein for each of the sides of the pillow:
when the baby's head is placed on the pillow and the side is used as a neck support, the pillow contacts the baby's head at an exclusive one of the plurality of different sets of contact points.

23. The pillow of claim 16, wherein the pillow has a top side and a bottom side;

wherein when the pillow is positioned with the top side facing up and the first one of the sides of the polygon is used as a neck support, the pillow contacts the baby's head at the first set of contact points; and wherein when the pillow is flipped so the top side is facing down and the first one of the sides of the polygon is used as a neck support, the pillow contacts the baby's head at a third set of contact points; and wherein the third set of contact points is different from the first set of contact points.

24. The pillow of claim 16, wherein each side of the polygon has a different length.

* * * * *